(12) United States Patent
Gupta

(10) Patent No.: US 8,475,418 B2
(45) Date of Patent: Jul. 2, 2013

(54) CLOSED SYSTEM FOR SURGICAL LIMB PREP

(76) Inventor: Amit Gupta, Prospect, KY (US)

( * ) Notice: Subject to any disclaimer, the term of this patent is extended or adjusted under 35 U.S.C. 154(b) by 246 days.

(21) Appl. No.: 12/779,270

(22) Filed: May 13, 2010

(65) Prior Publication Data

US 2010/0298787 A1   Nov. 25, 2010

Related U.S. Application Data

(60) Provisional application No. 61/179,473, filed on May 19, 2009.

(51) Int. Cl.
*A61M 35/00* (2006.01)

(52) U.S. Cl.
USPC ............................ 604/292; 604/293; 604/308

(58) Field of Classification Search
USPC ............ 604/2, 304; 602/3, 20–21, 61, 41–43, 602/48
See application file for complete search history.

(56) References Cited

U.S. PATENT DOCUMENTS

| | | |
|---|---|---|
| 246,454 A | 8/1881 | Bruen |
| 871,689 A | 11/1907 | Ganzhorn |
| 3,342,182 A | 9/1967 | Charos |
| 5,715,841 A | 2/1998 | Utecht |
| 5,975,082 A | 11/1999 | Dowdy |
| 5,986,162 A | 11/1999 | Dolisi |
| 6,635,035 B1 | 10/2003 | Marasco et al. |
| 2006/0064066 A1* | 3/2006 | Wang ............................ 604/292 |
| 2007/0026028 A1* | 2/2007 | Close et al. ................... 424/402 |
| 2008/0103461 A1* | 5/2008 | Johnson et al. ............... 604/292 |
| 2008/0119801 A1 | 5/2008 | Moore |

OTHER PUBLICATIONS

ISA/US, International Search Report and Written Opinion for related international application PCT/US10/34668, mailed Jul. 15, 2010.

* cited by examiner

*Primary Examiner* — Loan Thanh
*Assistant Examiner* — Andrew S Lo
(74) *Attorney, Agent, or Firm* — Stites & Harbison, PLLC; David W. Nagle, Jr.

(57) ABSTRACT

A closed system for surgical limb prep has: a two-layered construction, including an inner layer and a top layer; or a three-layered construction, including an inner layer, an intermediate layer, and a top layer. The inner layer fits over and engages the limb of the patient, and the inner layer also serves as a storage medium for a topical antiseptic or other prep fluid. The intermediate layer, if present, is positioned over the inner layer and is preferably made of a substantially waterproof or fluid-resistant material. The top layer covers the other layer(s) and includes one or more strips of adhesive that can be used to secure the top layer to the limb of the patient, effectively sealing and closing the system about the limb of the patient.

10 Claims, 9 Drawing Sheets

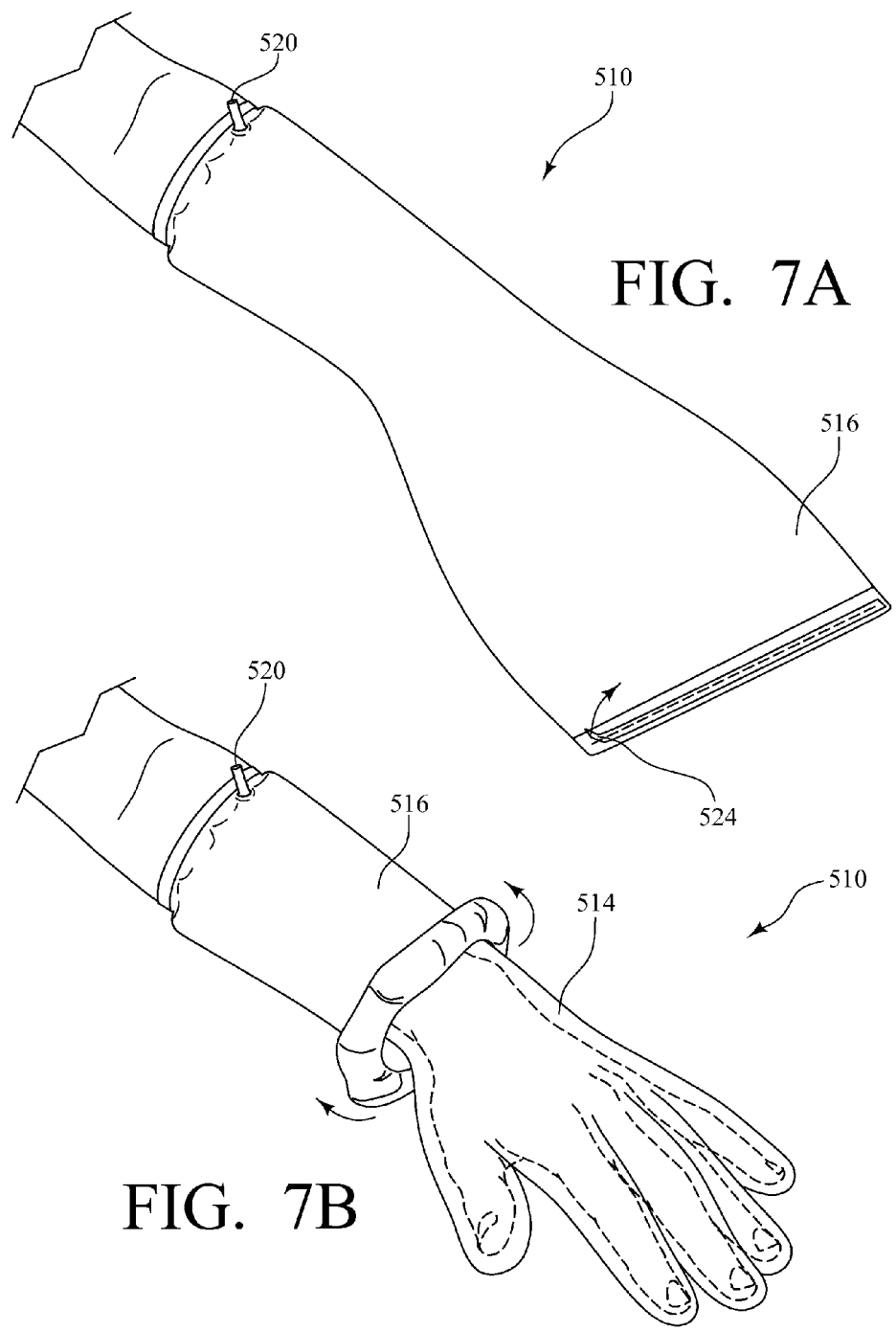

CLOSED SYSTEM FOR SURGICAL LIMB PREP

CROSS-REFERENCE TO RELATED APPLICATIONS

The present application claims priority to U.S. Provisional Patent Application Ser. No. 61/179,473 filed on May 19, 2009, the entire disclosure of which is incorporated herein by reference.

TECHNICAL FIELD

The present invention relates to preparing a limb (such as an arm or leg) for a surgical procedure, and, more specifically, to a closed system for surgical limb prep that reduces labor and reduces the use of operating room time.

BACKGROUND OF THE INVENTION

During a surgical procedure on a limb, it is of utmost importance to keep everything sterile to ensure the patient does not pick up any disease-causing germs. Therefore, prior to the surgical procedure, the limb is commonly "prepped" in the operating room by a nurse. In this prepping process, an assistant holds the limb, and a nurse then wipes the limb with a topical antiseptic, such as a chlorhexidine solution or Betadine®. (Betadine® is a registered trademark of Purdue Products, L.P. of Stamford, Conn.). Once the antiseptic dries, the limb is ready for the surgical procedure.

The disadvantage of this prepping process is that it requires using two persons, making the prep work labor-intensive. Furthermore, this prepping process requires about 20 to 30 minutes of operating room time, which significantly adds to the cost of the surgical procedure. In addition, this prepping process can also be messy.

Thus, there is a need for an improved system for surgical limb prep.

SUMMARY OF THE INVENTION

The present invention is a closed system for surgical limb prep that reduces labor and reduces the use of operating room time.

One exemplary closed system for surgical limb prep made in accordance with the present invention has a three-layered construction, including an inner layer, an intermediate layer, and a top layer. The inner layer fits over and engages the limb of the patient. Thus, the inner layer effectively covers the entire external surface of the limb. The inner layer also serves as a storage medium for a topical antiseptic or other prep fluid. Thus, the inner layer may be made of a sponge-like material with the topical antiseptic or other prep fluid impregnated in the sponge-like material. The intermediate layer is positioned over the inner layer and is preferably made of a substantially waterproof or fluid-resistant material. The top layer covers the intermediate layer and is preferably made of a material similar to that used in surgical gowns, i.e., certain non-woven materials that are also substantially waterproof or fluid-resistant. Furthermore, the top layer includes one or more strips of adhesive that can be used to secure the top layer to the limb of the patient, effectively sealing and closing the system about the limb of the patient.

The top layer also includes multiple tear strips (or pull tabs) that allow the top layer to be readily removed. Specifically, a user can tear and separate the top layer by using the multiple tear strips along its periphery, which then allows the top layer to be partially or entirely removed. Once the top layer has been removed, the intermediate layer becomes accessible. The intermediate layer may also include a tear strip to allow the intermediate layer to be separated and removed.

Another exemplary closed system for surgical limb prep made in accordance with the present invention has a two-layered construction, including an inner layer and a top layer. The inner layer is adhered to the internal surface of the top layer. This inner layer may be made of a sponge-like material with a topical antiseptic or other prep fluid impregnated in the sponge-like material, and the inner layer covers the entire external surface of the limb. The top layer also includes one or more strips of adhesive that can be used to secure the top layer to the limb of the patient, effectively sealing and closing the system about the limb of the patient.

Irrespective of the particular embodiment, the resultant system can be stored in a sterile package until use. In use, the system is applied to the limb of a patient in the pre-op area and prior to administration of a nerve-blocking anesthesia. Specifically, the system is placed over the limb and secured to the limb of the patient by the strips of adhesive, effectively sealing and closing the system about the limb of the patient. A circular band, which is preferably elastic, can then be moved up and down over the external surface of the top layer to apply pressure to the inner layer and spread the prep fluid over the skin of the patient. The patient is now prepped for the surgical procedure. In the operating room, excess prep fluid is removed. The top layer is partially or entirely removed, and the area around the site of the surgical procedure is then draped with a surgical gown. The remaining layers are then removed to expose the site of the surgical procedure.

DESCRIPTION OF THE DRAWINGS

FIG. 7A is a perspective view of another exemplary closed system for surgical limb prep in accordance with the present invention;

FIG. 7B is a perspective view of the system of FIG. 7A, illustrating the top layer being rolled back to expose the intermediate layer;

DETAILED DESCRIPTION OF THE INVENTION

The present invention is a closed system for surgical limb prep that reduces labor and reduces the use of operating room time.

Figure 1A:
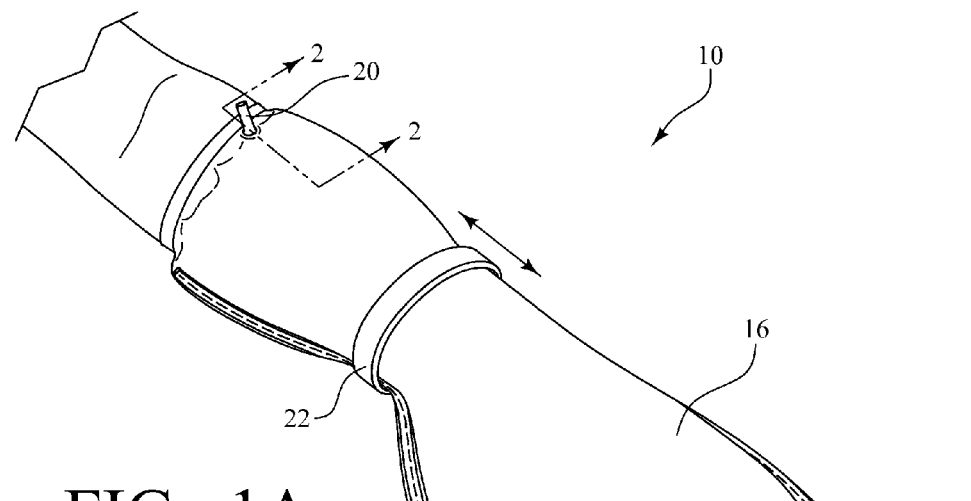
FIG. 1A is a perspective view of an exemplary closed system for surgical limb prep in accordance with the present invention.
Figure 1B:
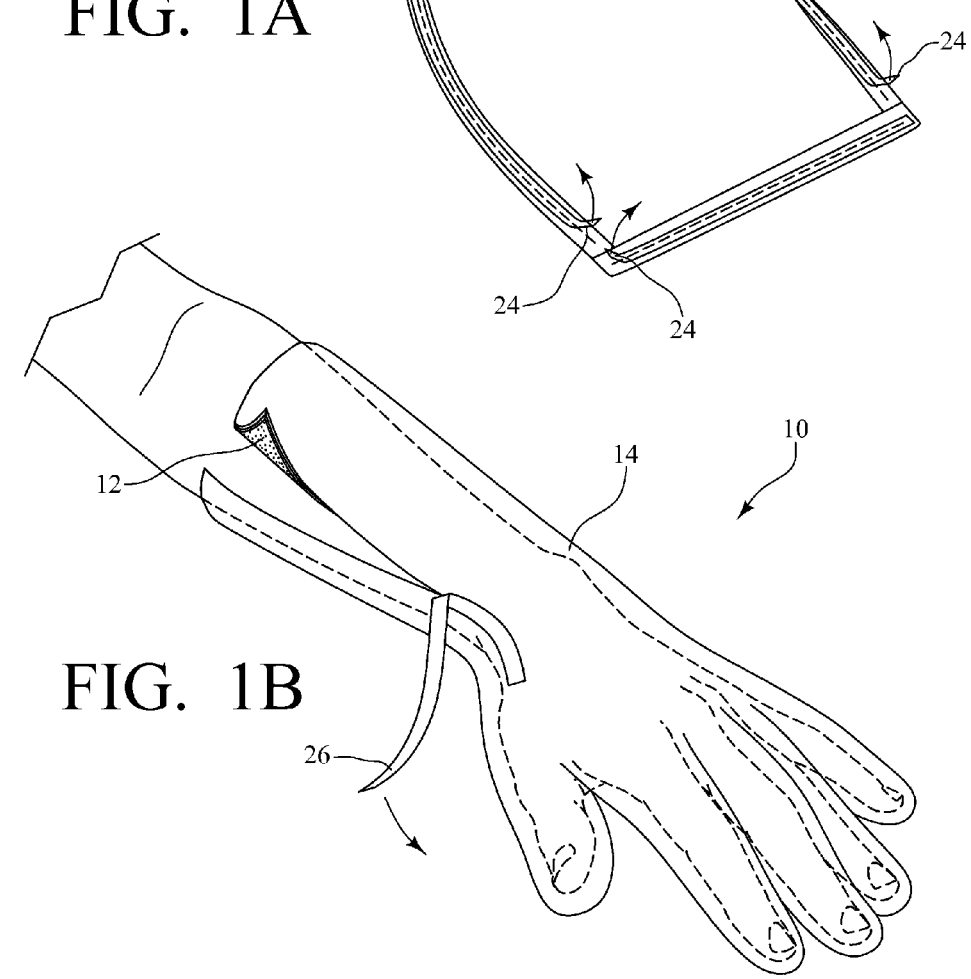
FIG. 1B is a perspective view of the system of FIG. 1A, illustrating the top layer removed and the intermediate layer in the process of being removed.
Figure 2:
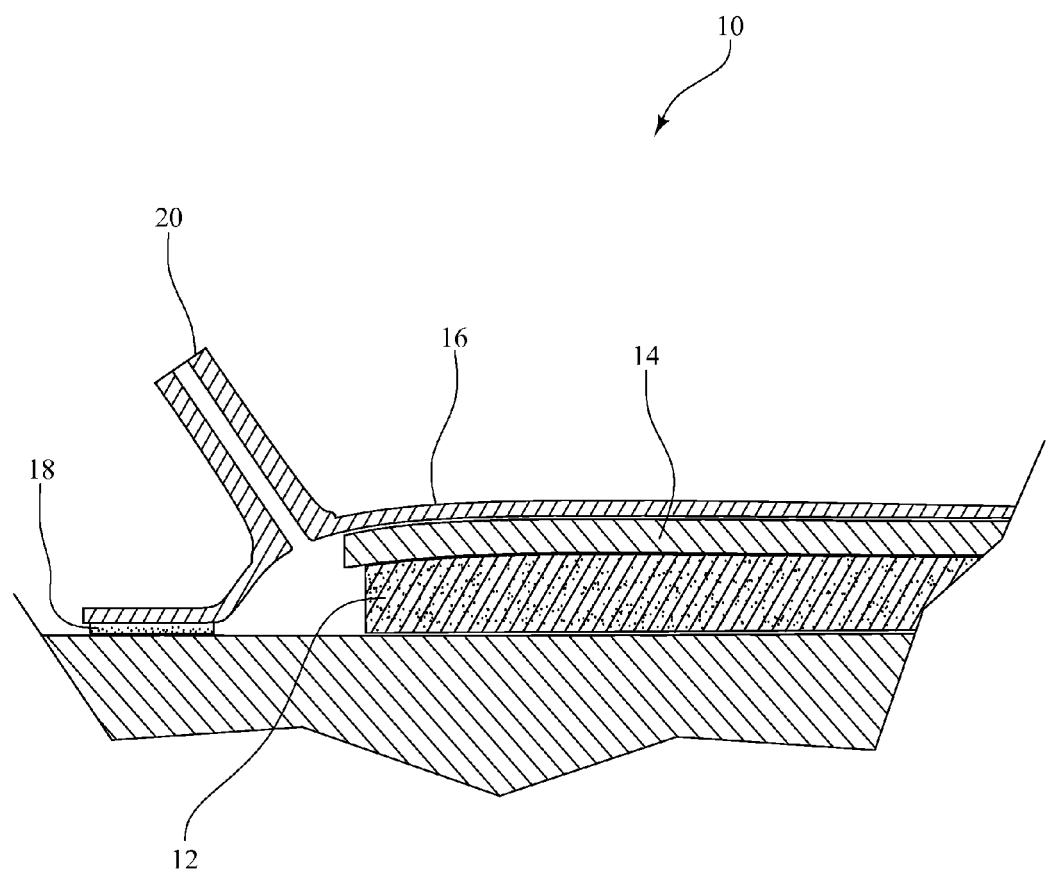
FIG. 2 is a cross-sectional view of the system of FIG. 1A, taken along line 2-2 of FIG. 1A.

Referring first to FIGS. 1A, 1B, and 2, an exemplary closed system for surgical limb prep made in accordance with the present invention, as generally indicated by reference numeral 10, has a three-layered construction, including an inner layer 12, an intermediate layer 14, and a top layer 16. In this exemplary embodiment, the inner layer 12 is in the shape of a glove that fits over and engages the hand and forearm of the patient. Thus, the inner layer 12 effectively covers the entire external surface of the hand and forearm, while also engaging the individual fingers. The inner layer 12 also serves as a storage medium for a topical antiseptic (such as a chlorhexidine solution or Betadine®) or other prep fluid. Specifically, in this exemplary embodiment, the inner layer 12 is made of a sponge-like material with the topical antiseptic or other prep fluid impregnated in the sponge-like material, the importance of which is further described below.

As best shown in FIGS. 1B and 2, the intermediate layer 14 is positioned over the inner layer 12 and is also in the shape of a glove that fits over and engages the hand and forearm of the patient. This intermediate layer 14 is preferably made of a substantially waterproof or fluid-resistant material, such a plastic material, to prevent any leakage of the prep fluid. Furthermore, in this exemplary embodiment, the intermediate layer 14 is adhered to the inner layer using a glue or similar adhesive.

Referring now to FIG. 2, the top layer 16 covers the intermediate layer 14. The top layer 16 is preferably made of a material similar to that used in surgical gowns, i.e., certain non-woven materials that are substantially waterproof or fluid-resistant. Furthermore, in this exemplary embodiment, the top layer 16 includes one or more strips of adhesive 18 (such as tape) that can be used to secure the top layer 16 to the arm of the patient, effectively sealing and closing the system about the arm of the patient. As a further refinement, a backing of some form (not shown) can be placed on the adhesive 18 to cover the adhesive 18 until the system 10 is positioned over the arm of the patient and is ready to be secured to the patient.

Referring still to FIG. 2, in this exemplary embodiment, the top layer 16 further includes a tube 20 that selectively places the interior of the system in fluid communication with the atmosphere. Since most operating rooms have access to a vacuum system, the tube 20 can be connected to such a vacuum system to suction out the excess prep fluid after the prepping is completed, as is further described below. Accordingly, the tube 20 preferably includes a one-way valve to allow prep fluid to be removed, while preventing any contamination from entering through the tube 20, thus maintaining the closed system.

Referring again to FIG. 1A, in this exemplary embodiment, a circular band 22 is placed over the top layer 16 and can be moved up and down over the external surface of the top layer 16 to apply pressure to the inner layer 12 and spread the prep fluid over the arm and hand of the patient, as is further described below. The band 22, which is preferably made of rubber or similar elastic material, can also be used to squeeze excess prep fluid toward the tube 20 to facilitate removal of the fluid.

In this exemplary embodiment, the top layer 16 further includes multiple tear strips (or pull tabs) 24 along its periphery, as shown in FIG. 1A, that allow the top layer 16 to be readily removed. Specifically, a user can tear and separate the top layer by using the multiple tear strips 24, which then allows the top layer 16 to be partially or entirely removed. Once the top layer 16 has been removed, the intermediate layer 14 is exposed and becomes accessible, as shown in FIG. 1B. In this exemplary embodiment, the intermediate layer 14 also includes a tear strip 26 to allow the intermediate layer 14 and the inner layer 12 (which is adhered to the intermediate layer 14) to be separated and removed.

Figure 3:
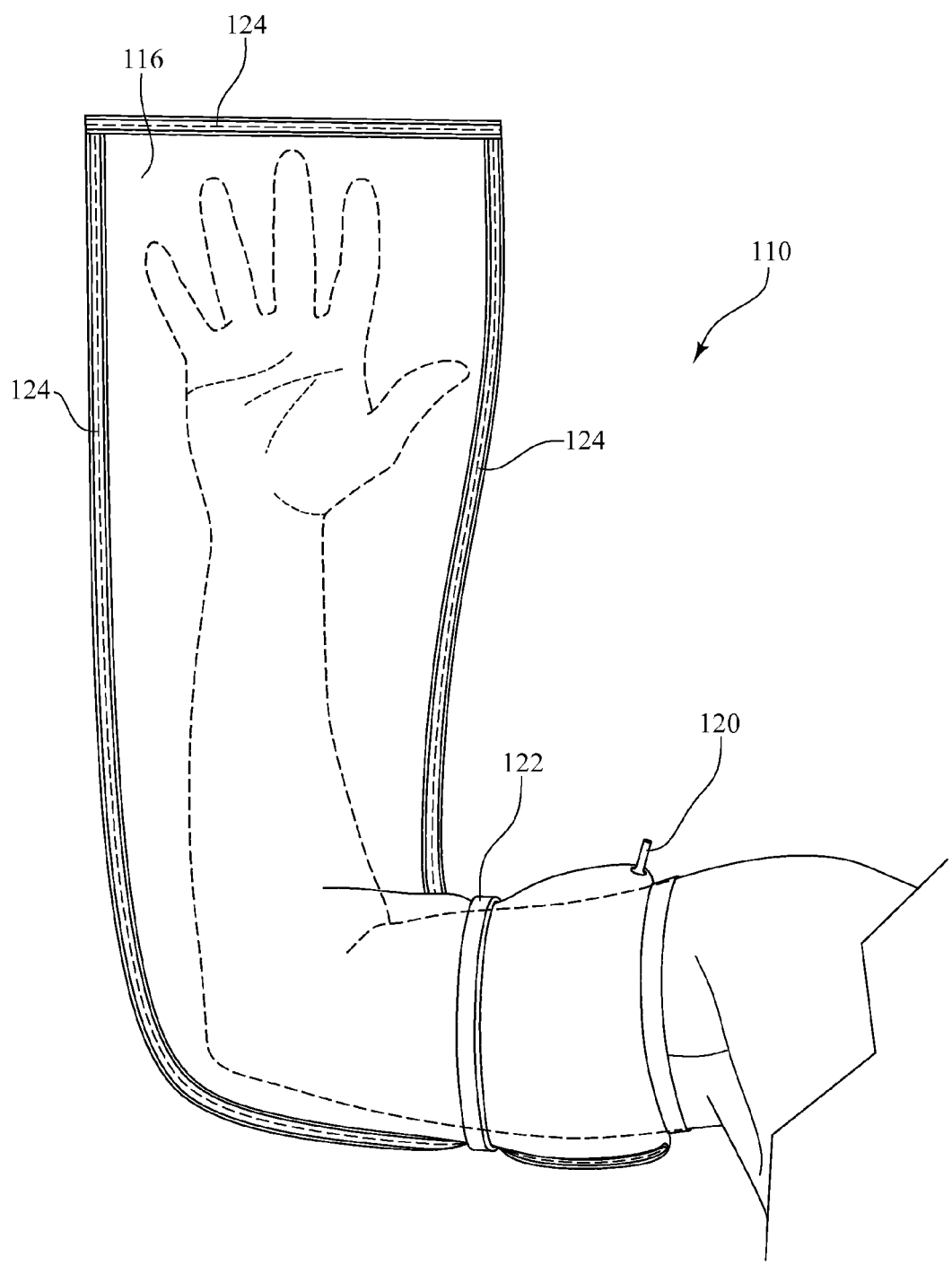
FIG. 3 is a perspective view of another exemplary closed system for surgical limb prep in accordance with the present invention.

FIG. 3 is a perspective view of another exemplary closed system 110 for surgical limb prep in accordance with the present invention. This exemplary closed system 110 is substantially identical to that illustrated in FIGS. 1A, 1B, and 2 and described above, except that it is sized and shaped to extend past the elbow of a patient. Thus, this exemplary closed system 110 would be useful not only for surgical procedures on the hand or wrist, but also for surgical procedures on the forearm and elbow of the patient. This exemplary closed system 110 also has a three-layered construction, including an inner layer, an intermediate layer, and a top layer 116. The top layer 116 includes a tube 120 that selectively places the interior of the system in fluid communication with the atmosphere. There is a circular band 122 placed over the top layer 116 that can be moved up and down over the external surface of the top layer 116 to apply pressure to the inner layer and spread the prep fluid over the arm and hand of the patient. Finally, the top layer 116 also includes multiple tear strips 124 along its periphery that allow the top layer 116 to be separated and removed.

Figure 4:
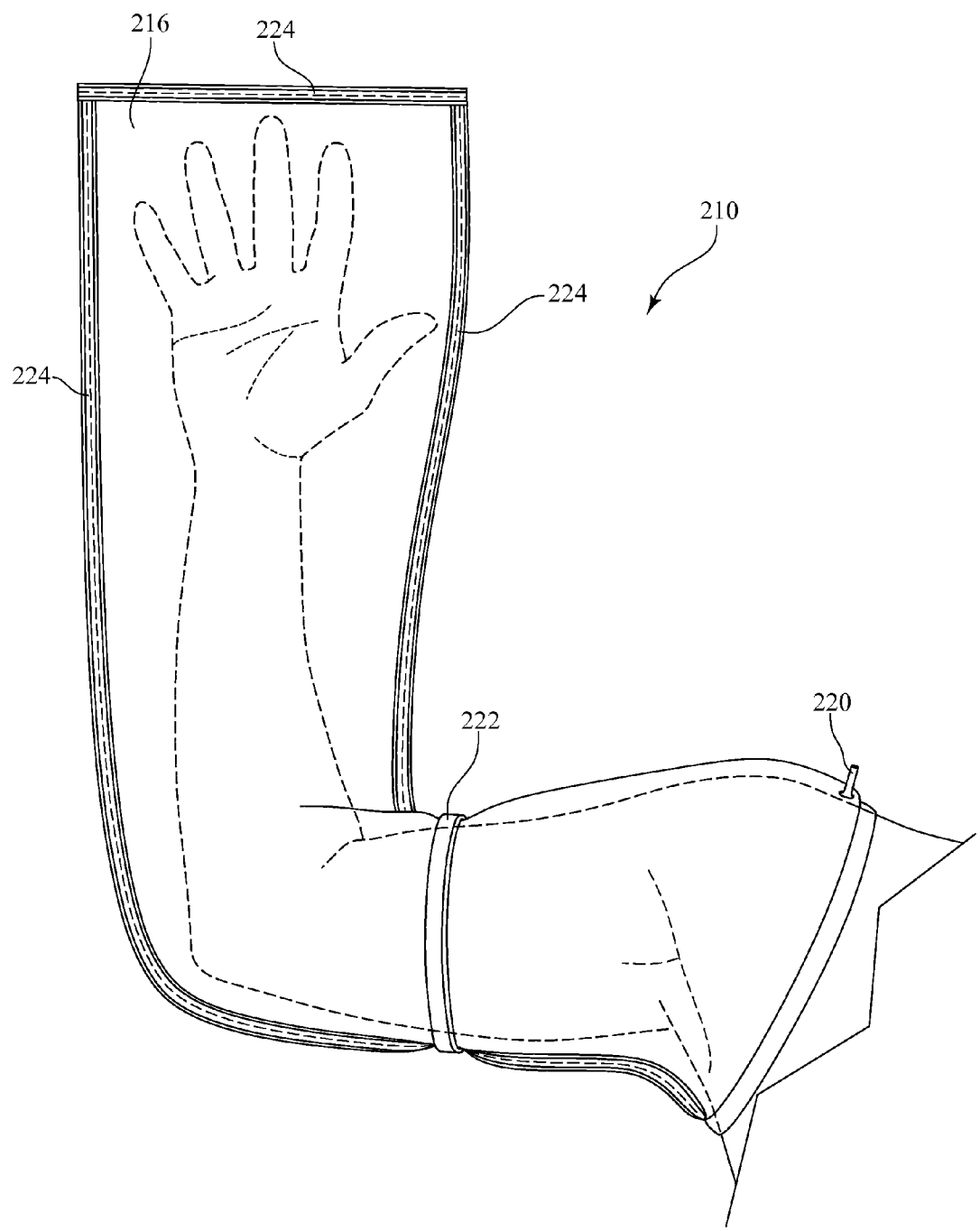
FIG. 4 is a perspective view of another exemplary closed system for surgical limb prep in accordance with the present invention, which is substantially identical to that illustrated in FIG. 3, but extends to the shoulder of the patient.

FIG. 4 is a perspective view of another exemplary closed system 210 for surgical limb prep in accordance with the present invention. This exemplary closed system 210 is substantially identical to that illustrated in FIG. 3 and described above, except that it is sized and shaped to extend to the shoulder of the patient. Thus, this exemplary closed system 210 would be useful for surgical procedures anywhere along arm of the patient, including the shoulder. This exemplary closed system 210 also has a three-layered construction, including an inner layer, an intermediate layer, and a top layer 216. The top layer 216 includes a tube 220 that selectively places the interior of the system in fluid communication with the atmosphere. There is a circular band 222 placed over the top layer 216 that can be moved up and down over the external surface of the top layer 216 to apply pressure to the inner layer and spread the prep fluid over the arm and hand of the patient. Finally, the top layer 216 also includes multiple tear strips 224 along its periphery that allow the top layer 216 to be separated and removed.

Figure 5:
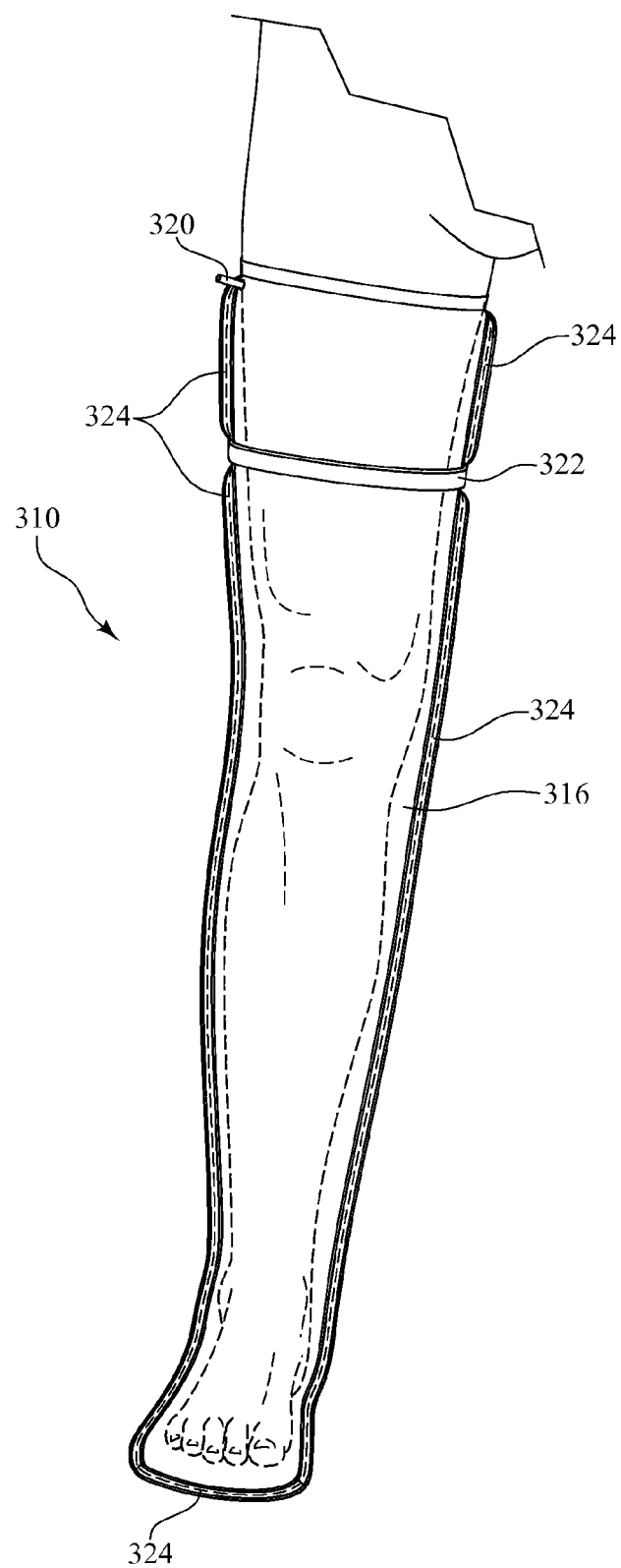
FIG. 5 is a perspective view of another exemplary closed system for surgical limb prep in accordance with the present invention.

FIG. 5 is a perspective view of another exemplary closed system 310 for surgical limb prep in accordance with the present invention, in which the exemplary closed system 310 is sized and shaped for the leg of a patient. Thus, this exemplary closed system 310 would be useful not only for surgical procedures on the foot or lower leg, but also for surgical procedures on or around the knee of the patient. As with the exemplary embodiment illustrated in FIGS. 1A, 1B, and 2 and described above, this exemplary closed system 310 has a three-layered construction, including an inner layer, an intermediate layer, and a top layer 316. Of course, in this exemplary embodiment, the inner layer is in the shape of a sock that fits over and engages the foot and lower leg of the patient.

Thus, the inner layer effectively covers the entire external surface of the foot and lower leg of the patient, while also engaging the individual toes. The top layer 316 includes a tube 320 that selectively places the interior of the system in fluid communication with the atmosphere. There is a circular band 322 placed over the top layer 316 that can be moved up and down over the external surface of the top layer 316 to apply pressure to the inner layer and spread the prep fluid over the leg and foot of the patient. Finally, the top layer 316 also includes multiple tear strips 324 along its periphery that allow the top layer 316 to be separated and removed.

Figure 6:
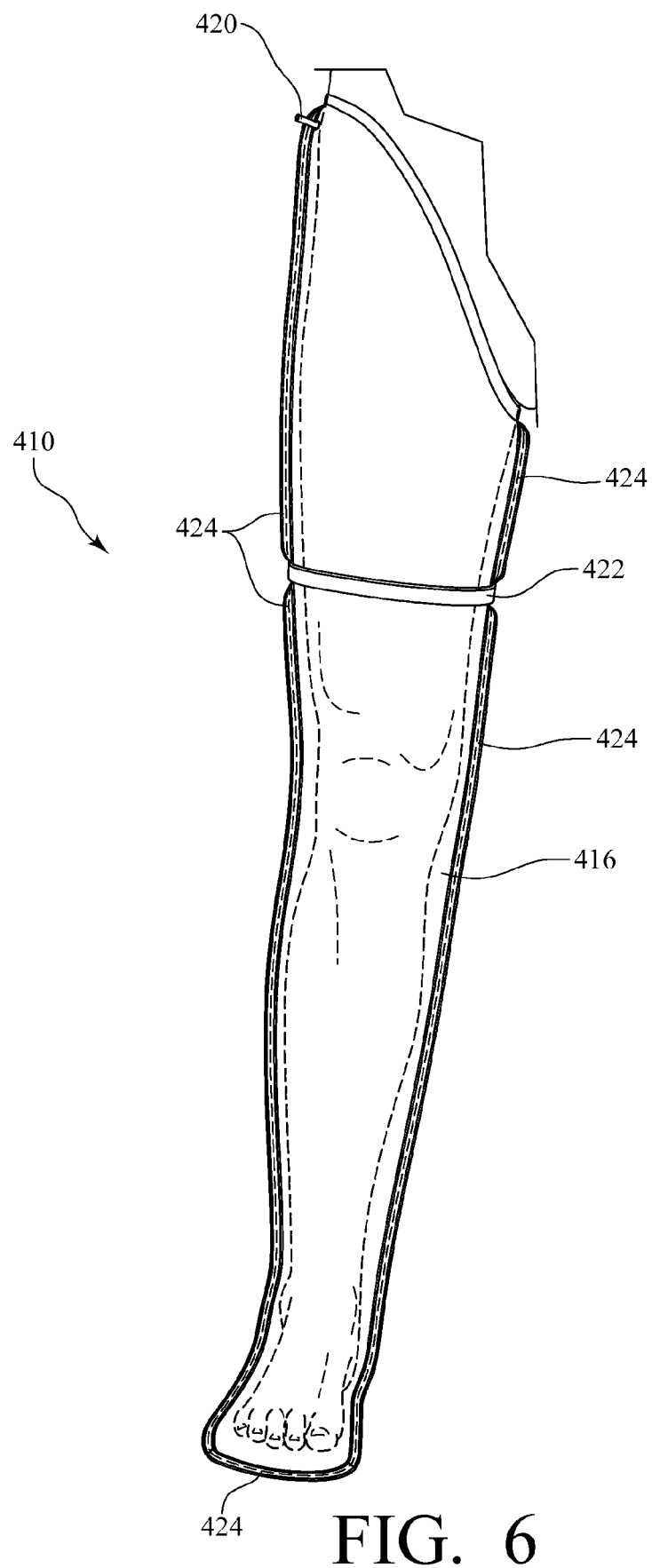
FIG. 6 is a perspective view of another exemplary closed system for surgical limb prep in accordance with the present invention, which is substantially identical to that illustrated in FIG. 5, but extends to the hip of the patient.

FIG. 6 is a perspective view of another exemplary closed system 410 for surgical limb prep in accordance with the present invention. This exemplary closed system 410 is substantially identical to that illustrated in FIG. 5 and described above, except that it is sized and shaped to extend to the hip of the patient. Thus, this exemplary closed system 410 would be useful for surgical procedures anywhere along the leg of the patient, including the hip area. This exemplary closed system 410 also has a three-layered construction, including an inner layer, an intermediate layer, and a top layer 416. The top layer 416 includes a tube 420 that selectively places the interior of the system in fluid communication with the atmosphere. There is a circular band 422 placed over the top layer 416 that can be moved up and down over the external surface of the top layer 416 to apply pressure to the inner layer and spread the prep fluid over the leg and foot of the patient. Finally, the top layer 416 also includes multiple tear strips 424 along its periphery that allow the top layer 416 to be separated and removed.

FIGS. 7A and 7B are views of another exemplary closed system 510 for surgical limb prep in accordance with the present invention. This exemplary closed system 510 is similar to the exemplary system 10 illustrated in FIGS. 1A, 1B, and 2, including a tube 520 that selectively places the interior of the system in fluid communication with the atmosphere; however, this exemplary closed system 510 only has a tear strip 524 located at the distal end of the top layer 516 near the fingers of the patient. Once the tear strip 524 has been torn away, the top layer 516 can then be rolled back to access the intermediate layer 514, as shown in FIG. 7B.

Figures 8A, 8B:
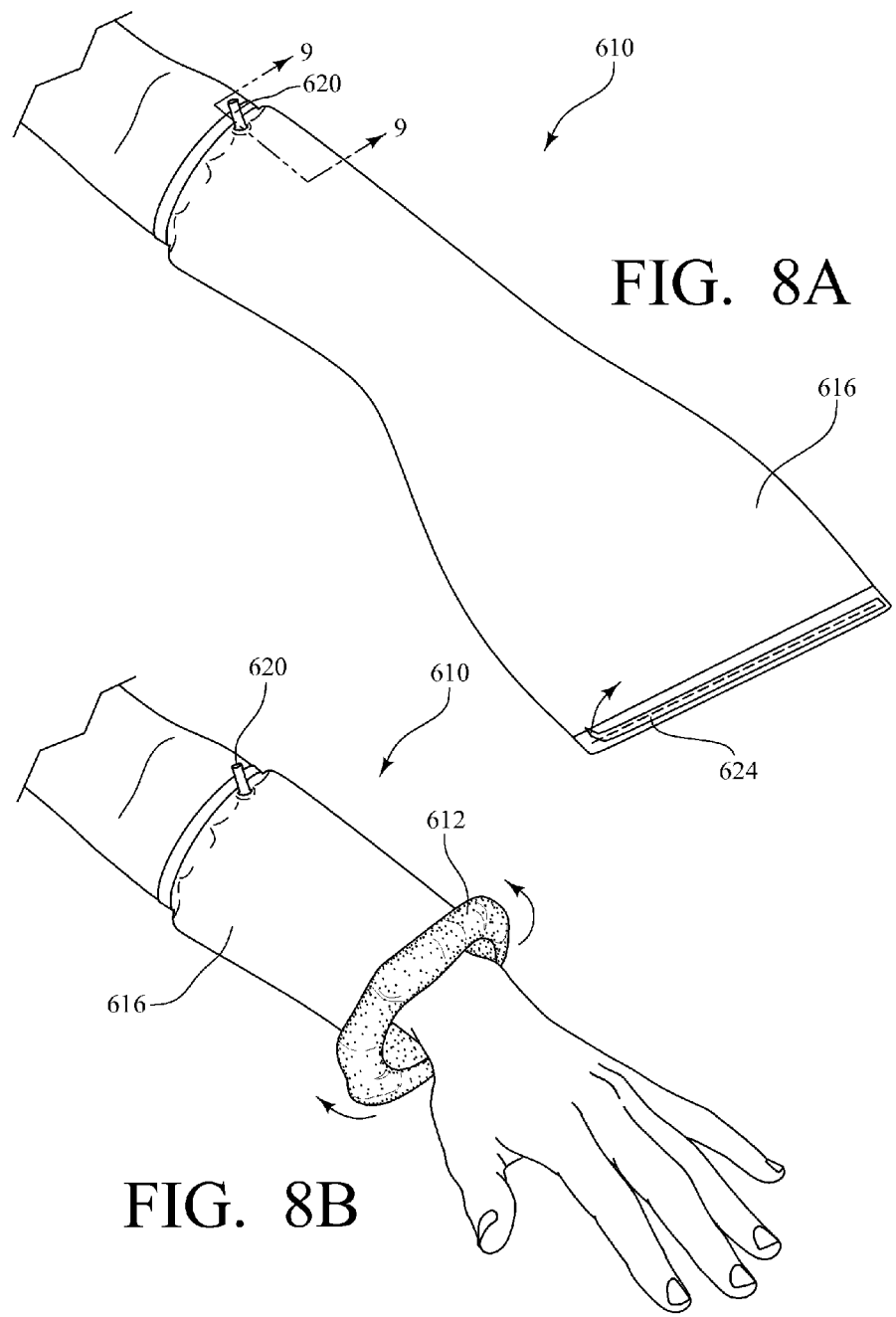
FIG. 8A is a perspective view of another exemplary closed system for surgical limb prep in accordance with the present invention.
FIG. 8B is a perspective view of the system of FIG. 8A, illustrating the top layer and the inner layer being rolled back to expose the limb.
Figure 9:
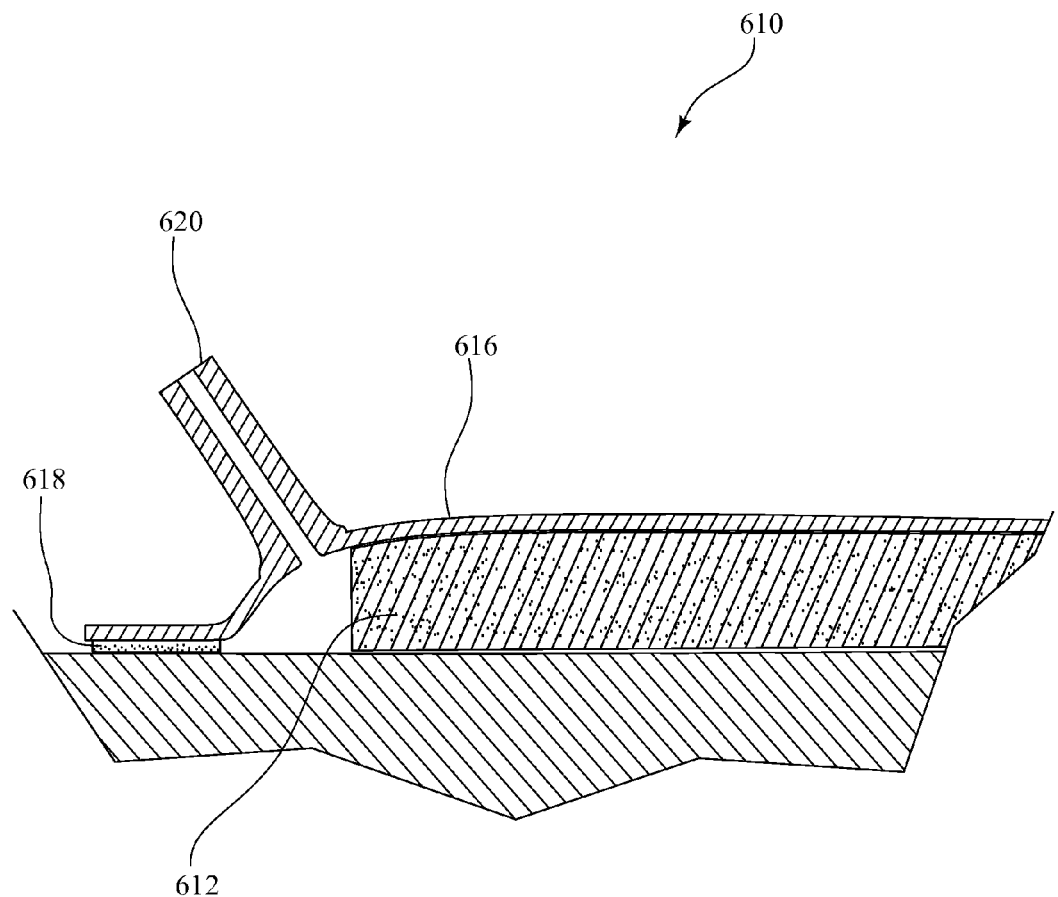
FIG. 9 is a cross-sectional view of the system of FIG. 8A, taken along line 9-9 of FIG. 8A.

FIGS. 8A, 8B and 9 are views of another exemplary closed system 610 for surgical limb prep in accordance with the present invention. This exemplary closed system 610 is similar to the exemplary closed system 610 illustrated in FIGS. 7A and 7B; however, this exemplary closed system 610 only has an inner layer 612 and a top layer 616; it does not have an intermediate layer. In other words, this exemplary closed system 610 has only a two-layered construction. The inner layer 612 is adhered to the internal surface of the top layer 616. This inner layer 612 still is made of a sponge-like material with a topical antiseptic or other prep fluid impregnated in the sponge-like material, and the inner layer 612 still covers the entire external surface of the hand and forearm. The top layer 616 also includes one or more strips of adhesive 618 (such as tape) that can be used to secure the top layer 616 to the arm of the patient, effectively sealing and closing the system about the arm of the patient. Furthermore, as with the various embodiments described above, the top layer 616 further includes a tube 620 that selectively places the interior of the system in fluid communication with the atmosphere. Finally, a circular band 622 is placed over the top layer 616 and can be moved up and down over the external surface of the top layer 616 to apply pressure to the inner layer 612 and spread the prep fluid over the leg and foot of the patient.

Referring to FIGS. 8A and 8B, in this exemplary embodiment, the exemplary closed system 610 has a tear strip 624 located at the distal end of the top layer 616 near the fingers of the patient. The top layer 616 can thus be rolled back similar to the embodiment illustrated in FIGS. 7A and 7B and described above. However, since there is no intermediate layer, and the inner layer 612 is adhered to the top layer 616, the inner layer 612 is rolled back with the top layer 616.

Irrespective of the particular embodiment, the resultant system can be stored in a sterile package until use. In use, the system is applied to the limb of a patient in the pre-op area and prior to administration of a nerve-blocking anesthesia. Specifically, the system is placed over the limb and secured to the limb of the patient by the strips of adhesive, effectively sealing and closing the system about the limb of the patient. The circular band can then be moved up and down over the external surface of the top layer to apply pressure to the inner layer and spread the prep fluid over the skin of the patient. The patient is now prepped for the surgical procedure. In the operating room, excess prep fluid is removed. The top layer is partially or entirely removed to expose the sterile intermediate layer (if present). The area around the site of the surgical procedure is then draped with a surgical gown. The remaining layers are then removed to expose the site of the surgical procedure.

One of ordinary skill in the art will recognize that additional embodiments are also possible without departing from the teachings of the present invention. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A closed system for surgical limb prep, comprising:
   an inner layer configured to fit over and cover an external surface of a limb of a patient, said inner layer storing a prep fluid;
   an intermediate layer positioned over the inner layer, said intermediate layer made from a fluid-resistant material;
   a top layer positioned over and covering the intermediate layer, said top layer configured to be secured to the limb of the patient, effectively sealing and closing the system about the limb of the patient; and
   one or more tear strips along a periphery of the top layer, allowing the top layer to be separated along the tear strips and partially or entirely removed, thus exposing the intermediate layer.

2. The closed system for surgical limb prep as recited in claim 1, and further comprising one or more tear strips along a periphery of the intermediate layer, allowing the intermediate layer to be separated along the tear strips and removed.

3. A closed system for surgical limb prep, comprising:
   an inner layer configured to fit over and cover an external surface of a limb of a patient, said inner layer storing a prep fluid;
   an intermediate layer positioned over the inner layer, said intermediate layer made from a fluid-resistant material;
   a top layer positioned over and covering the intermediate layer, said top layer configured to be secured to the limb of the patient, effectively sealing and closing the system about the limb of the patient; and
   a tear strip located at a distal end of the top layer, allowing the top layer to be separated along the tear strip and then rolled back to access the intermediate layer.

4. A closed system for surgical limb prep, comprising:
an inner layer configured to fit over and cover an external surface of a limb of a patient, said inner layer storing a prep fluid;
a top layer positioned over and covering the inner layer, said top layer configured to be secured to the limb of the patient, effectively sealing and closing the system about the limb of the patient; and
one or more tear strips along a portion of a periphery of the top layer allowing the top layer to be separated along the tear strips and partially or entirely removed, thus exposing the inner layer.

5. The closed system for surgical limb prep as recited in claim 4, wherein the inner layer is adhered to an internal surface of the top layer.

6. The closed system for surgical limb prep as recited in claim 4, wherein the inner layer is made of a sponge-like material with the prep fluid impregnated in the sponge-like material.

7. The closed system for surgical limb prep as recited in claim 4, and further comprising one or more strips of adhesive for securing the top layer to the limb of the patient.

8. The closed system for surgical limb prep as recited in claim 4, and further comprising a tube that selectively places the interior of the closed system in fluid communication with the atmosphere.

9. The closed system for surgical limb prep as recited in claim 4, and further comprising a circular band that is placed over the top layer and can be moved up and down over the external surface of the top layer to apply pressure to the inner layer and spread the prep fluid over the limb of the patient.

10. The closed system for surgical limb prep as recited in claim 9, in which the circular band is elastic.

* * * * *